US012716081B2

(12) United States Patent
Kim et al.

(10) Patent No.: US 12,716,081 B2
(45) Date of Patent: Aug. 25, 2026

(54) MUTANT OF CORYNEBACTERIUM GLUTAMICUM WITH ENHANCED L-CITRULLINE PRODUCTIVITY AND METHOD FOR PREPARING L-CITRULLINE USING THE SAME

(71) Applicant: DAESANG CORPORATION, Seoul (KR)

(72) Inventors: Moon Jeong Kim, Gyeongsangbuk-do (KR); Dong Seok Lee, Gyeonggi-do (KR); Sun Jun Yoon, Gyeonggi-do (KR); Seok Hyun Park, Gyeonggi-do (KR); Joon Hyun Park, Gyeonggi-do (KR)

(73) Assignee: DAESANG CORPORATION, Seoul (KR)

( * ) Notice: Subject to any disclaimer, the term of this patent is extended or adjusted under 35 U.S.C. 154(b) by 298 days.

(21) Appl. No.: 18/280,846

(22) PCT Filed: Jan. 19, 2022

(86) PCT No.: PCT/KR2022/000971
§ 371 (c)(1),
(2) Date: Oct. 3, 2023

(87) PCT Pub. No.: WO2022/196919
PCT Pub. Date: Sep. 22, 2022

(65) Prior Publication Data

US 2024/0150801 A1 May 9, 2024

(30) Foreign Application Priority Data

Mar. 17, 2021 (KR) ........................ 10-2021-0034544

(51) Int. Cl.
*C12P 13/10* (2006.01)
*C12N 9/10* (2006.01)

(52) U.S. Cl.
CPC ............ *C12P 13/10* (2013.01); *C12N 9/1029* (2013.01); *C12Y 203/01008* (2013.01)

(58) Field of Classification Search
CPC ....... C12P 13/10; C12N 9/1029; C12N 15/77; C12Y 203/01008; C12R 2001/15
See application file for complete search history.

(56) References Cited

FOREIGN PATENT DOCUMENTS

| | | |
|---|---|---|
| CN | 102498216 | 6/2012 |
| EP | 2 471 943 | 7/2012 |
| JP | 2014-517681 | 7/2014 |
| JP | 2016-163540 | 9/2016 |
| KR | 10-1053429 | 8/2011 |
| KR | 10-1102263 | 1/2012 |

OTHER PUBLICATIONS

Reinscheid et al., Microbiology 145:503-513, 1999.*
International Search Report issued Jun. 20, 2022 in International (PCT) Application No. PCT/KR2022/000971, 8 pages.
Zhang, B. et al., "Optimization of L-ornithine production in recombinant Corynebacterium glutamicum S9114 by cg3035 overexpression and manipulating the central metabolic pathway", Microbial Cell Factories. 2018, vol. 17, Article No. 91, pp. 1-13.
GenBank. C. glutamicum pta gene and ackA gene. Accession No. X89084.1 (publication date: Apr. 18, 2005).
Wu, Xiao-Yu et al., "Recent Advances of L-ornithine Biosynthesis in Metabolically Engineered Corynebacterium glutamicum", Frontiers in Bioengineering and Biotechnology, 2020, vol. 7, Article 440, pp. 1-12.
Stansen, C. et al., "Characterization of a Corynebacterium glutamicum Lactate Utilization Operon Induced during Temperature-Triggered Glutamate Production", Applied and Environmental Microbiology, 2005, vol. 71, pp. 5920-5928.
Office Action issued Sep. 17, 2024 in Japanese Patent Application No. 2023-557193, with English-language Translation.
Office Action issued May 22, 2026 in corresponding Chinese Patent Application No. 202280021948.8, with English translation, 17 pages.
Dieter J. Reinscheid et al., "Cloning, sequence analysis, expression and inactivation of the *Corynebacterium glutamicum pta-ack* operon encoding phosphotransacetylase and acetate kinase", Microbiology, 1999, vol. 145, pp. 503-513, 11 pages.
Jaide V.K. Jensen et al., "Modular pathway engineering of *Corynebacterium glutamicum* for production of the glutamate-derived compounds ornithine, proline, putrescine, citrulline, and arginine", Journal of Biotechnology, 2015, vol. 2, pp. 85-94, 10 pages.
Bin Zhang et al., "Optimization of L-ornithine production in recombinant *Corynebacterium glutamicum* S9114 by cg3035 overexpression and manipulating the central metabolic pathway", Micro Cel Fact, 2018, 17:91, 13 pages.

* cited by examiner

*Primary Examiner* — Delia M Ramirez
(74) *Attorney, Agent, or Firm* — Wenderoth, Lind & Ponack, L.L.P.

(57) ABSTRACT

The present invention relates to a *Corynebacterium glutamicum* mutant strain having increased L-citrulline productivity, and a method of producing L-citrulline using the same. The *Corynebacterium glutamicum* mutant strain is capable of producing L-citrulline in high yield and high concentration while inhibiting the production of by-products, because the activity of the protein that is expressed by the NCgl2657 gene therein has been weakened or inactivated.

3 Claims, No Drawings

Specification includes a Sequence Listing.

SEQUENCE LISTING

```
<160> NUMBER OF SEQ ID NOS: 10

<210> SEQ ID NO 1
<211> LENGTH: 1386
<212> TYPE: DNA
<213> ORGANISM: Artificial Sequence
<220> FEATURE:
<223> OTHER INFORMATION: NCgl2657 gene

<400> SEQUENCE: 1

atgtctgaca caccgacctc agctctgatc accacggtca accgcagctt cgatggattc      60

gatttggaag aagtagcagc agaccttgga gttcggctca cctacctgcc cgacgaagaa     120

ctagaagtat ccaaagttct cgcggcggac ctcctcgctg aggggccagc tctcatcatc     180
```

```
ggtgtaggaa acacgttttt cgacgcccag gtcgccgctg ccctcggcgt cccagtgcta    240
ctgctggtag acaagcaagg caagcacgtt gctcttgctc gcacccaggt aaacaatgcc    300
ggcgcagttg ttgcagcagc atttaccgct gaacaagagc caatgccgga taagctgcgc    360
aaggctgtgc gcaaccacag caacctcgaa ccagtcatga gcgccgaact ctttgaaaac    420
tggctgctca agcgcgcacg cgcagagcac tcccacattg tgctgccaga aggtgacgac    480
gaccgcatct tgatggctgc ccaccagctg cttgatcaag acatctgtga catcacgatc    540
ctgggcgatc cagtaaagat caaggagcgc gctaccgaac ttggcctgca ccttaacact    600
gcatacctgg tcaatccgct gacagatcct cgcctggagg aattcgccga acaattcgcg    660
gagctgcgca agtcaaagag cgtcactatc gatgaagccc gcgaaatcat gaaggatatt    720
tcctacttcg gcaccatgat ggtccacaac ggcgacgccg acggaatggt atccggtgca    780
gcaaacacca ccgcacacac cattaagcca agcttccaga tcatcaaaac tgttccagaa    840
gcatccgtcg tttcttccat cttcctcatg gtgctgcgcg ggcgactgtg ggcattcggc    900
gactgtgctg ttaacccgaa cccaactgct gaacagcttg gtgaaatcgc cgttgtgtca    960
gcaaaaactg cagcacaatt tggcattgat cctcgcgtag ccatcttgtc ctactccact   1020
ggcaactccg gcggaggctc agatgtggat cgcgccatcg acgctcttgc agaagcacgc   1080
cgacttaacc cagaactatg cgtcgatgga ccacttcagt tcgacgccgc cgtcgacccg   1140
ggtgtggcgc gcaagaagat gccagactct gacgtcgctg gccaggcaaa tgtgtttatc   1200
ttccctgacc tggaagccgg aaacatcggc tacaaaactg cacaacgcac cggtcacgcc   1260
ctggcagttg gtccgattct gcagggccta aacaaaccag tcaacgacct ttcccgtggc   1320
gcaacagtcc ctgacatcgt caacacagta gccatcacag caattcaggc aggaggacgc   1380
agctaa                                                              1386
```

<210> SEQ ID NO 2
<211> LENGTH: 1386
<212> TYPE: DNA
<213> ORGANISM: Artificial Sequence
<220> FEATURE:
<223> OTHER INFORMATION: NCgl2657 gene - substituted ATG with TTG

<400> SEQUENCE: 2

```
ttgtctgaca caccgacctc agctctgatc accacggtca accgcagctt cgatggattc     60
gatttggaag aagtagcagc agaccttgga gttcggctca cctacctgcc cgacgaagaa    120
ctagaagtat ccaaagttct cgcggcggac ctcctcgctg aggggccagc tctcatcatc    180
ggtgtaggaa acacgttttt cgacgcccag gtcgccgctg ccctcggcgt cccagtgcta    240
ctgctggtag acaagcaagg caagcacgtt gctcttgctc gcacccaggt aaacaatgcc    300
ggcgcagttg ttgcagcagc atttaccgct gaacaagagc caatgccgga taagctgcgc    360
aaggctgtgc gcaaccacag caacctcgaa ccagtcatga gcgccgaact ctttgaaaac    420
tggctgctca agcgcgcacg cgcagagcac tcccacattg tgctgccaga aggtgacgac    480
gaccgcatct tgatggctgc ccaccagctg cttgatcaag acatctgtga catcacgatc    540
ctgggcgatc cagtaaagat caaggagcgc gctaccgaac ttggcctgca ccttaacact    600
gcatacctgg tcaatccgct gacagatcct cgcctggagg aattcgccga acaattcgcg    660
gagctgcgca agtcaaagag cgtcactatc gatgaagccc gcgaaatcat gaaggatatt    720
tcctacttcg gcaccatgat ggtccacaac ggcgacgccg acggaatggt atccggtgca    780
gcaaacacca ccgcacacac cattaagcca agcttccaga tcatcaaaac tgttccagaa    840
```

gcatccgtcg tttcttccat cttcctcatg gtgctgcgcg ggcgactgtg ggcattcggc 900
gactgtgctg ttaacccgaa cccaactgct gaacagcttg gtgaaatcgc cgttgtgtca 960
gcaaaaactg cagcacaatt tggcattgat cctcgcgtag ccatcttgtc ctactccact 1020
ggcaactccg gcggaggctc agatgtggat cgcgccatcg acgctcttgc agaagcacgc 1080
cgacttaacc cagaactatg cgtcgatgga ccacttcagt tcgacgccgc cgtcgacccg 1140
ggtgtggcgc gcaagaagat gccagactct gacgtcgctg gccaggcaaa tgtgtttatc 1200
ttccctgacc tggaagccgg aaacatcggc tacaaaactg cacaacgcac cggtcacgcc 1260
ctggcagttg gtccgattct gcagggccta aacaaaccag tcaacgacct ttcccgtggc 1320
gcaacagtcc ctgacatcgt caacacagta gccatcacag caattcaggc aggaggacgc 1380
agctaa 1386

<210> SEQ ID NO 3
<211> LENGTH: 40
<212> TYPE: DNA
<213> ORGANISM: Artificial Sequence
<220> FEATURE:
<223> OTHER INFORMATION: chemically synthesized Primer 1

<400> SEQUENCE: 3
ctatgaccat gattacgcca cagtggagaa cacgatcgcg 40

<210> SEQ ID NO 4
<211> LENGTH: 40
<212> TYPE: DNA
<213> ORGANISM: Artificial Sequence
<220> FEATURE:
<223> OTHER INFORMATION: chemically synthesized Primer 2

<400> SEQUENCE: 4
gaggtcggtg tgtcagacaa acatcgcctt tctaatttca 40

<210> SEQ ID NO 5
<211> LENGTH: 40
<212> TYPE: DNA
<213> ORGANISM: Artificial Sequence
<220> FEATURE:
<223> OTHER INFORMATION: chemically synthesized Primer 3

<400> SEQUENCE: 5
tgaaattaga aaggcgatgt ttgtctgaca caccgacctc 40

<210> SEQ ID NO 6
<211> LENGTH: 40
<212> TYPE: DNA
<213> ORGANISM: Artificial Sequence
<220> FEATURE:
<223> OTHER INFORMATION: chemically synthesized Primer 4

<400> SEQUENCE: 6
gctcggtacc cggggatcct cggcgtcgcc gttgtggacc 40

<210> SEQ ID NO 7
<211> LENGTH: 40
<212> TYPE: DNA
<213> ORGANISM: Artificial Sequence
<220> FEATURE:
<223> OTHER INFORMATION: chemically synthesized Primer 5

<400> SEQUENCE: 7

-continued

```
ctatgaccat gattacgcca cagtggagaa cacgatcgcg                        40


<210> SEQ ID NO 8
<211> LENGTH: 40
<212> TYPE: DNA
<213> ORGANISM: Artificial Sequence
<220> FEATURE:
<223> OTHER INFORMATION: chemically synthesized Primer 6

<400> SEQUENCE: 8

caaaacaagt gccaatgcca acatcgcctt tctaatttca                        40


<210> SEQ ID NO 9
<211> LENGTH: 40
<212> TYPE: DNA
<213> ORGANISM: Artificial Sequence
<220> FEATURE:
<223> OTHER INFORMATION: chemically synthesized Primer 7

<400> SEQUENCE: 9

tgaaattaga aaggcgatgt tggcattggc acttgttttg                        40


<210> SEQ ID NO 10
<211> LENGTH: 40
<212> TYPE: DNA
<213> ORGANISM: Artificial Sequence
<220> FEATURE:
<223> OTHER INFORMATION: chemically synthesized Primer 8

<400> SEQUENCE: 10

gctcggtacc cggggatcct atcgatgctc atgccagcgg                        40
```

MUTANT OF CORYNEBACTERIUM GLUTAMICUM WITH ENHANCED L-CITRULLINE PRODUCTIVITY AND METHOD FOR PREPARING L-CITRULLINE USING THE SAME

TECHNICAL FIELD

The present invention relates to a *Corynebacterium glutamicum* mutant strain having increased L-citrulline productivity and a method of producing L-citrulline using the same.

BACKGROUND ART

L-citrulline is one of the non-essential amino acids, and it is known that citrulline has useful effects such as promoting ammonia metabolism, improving blood flow by vasodilation, lowering blood pressure, enhancing neurotransmission, enhancing immunity, and scavenging reactive oxygen species. Such citrulline is synthesized as an intermediate product during arginine biosynthesis. The biosynthesis of arginine in microorganisms proceeds from L-glutamate via eight enzymatic steps through two different pathways, a linear pathway and a cyclic pathway. In the linear pathway, L-arginine is synthesized from L-glutamate via N-acetylglutamate, N-acetylornithine, ornithine, citrulline, and argininosuccinate.

L-citrulline is generally produced by fermentation using microorganisms such as bacteria or yeast, and the production of L-citrulline may be performed using a naturally occurring wild-type strain or a mutant strain modified from the wild-type strain so as to have increased L-citrulline productivity. Recently, in order to improve the efficiency of production of L-citrulline, genetic recombination technology has been applied to microorganisms such as *Escherichia coli* and *Corynebacterium*, which have been widely used for the production of L-amino acids and other useful substances, and various recombinant strains or mutant strains having excellent L-citrulline productivity and methods of producing L-citrulline using the same have been developed. According to Korean Patent Nos. 10-1102263 and 10-1053429, it was confirmed that L-citrulline productivity is increased by enhancing or weakening the activities or expressions of proteins such as enzymes and transcription factors, which are involved in L-citrulline biosynthesis. Therefore, it may be expected that the production of L-citrulline may also be regulated by regulating the activities or expressions of various proteins, including enzymes involved in the L-citrulline biosynthetic pathway.

Prior Art Documents

Patent Documents

Korean Patent No. 10-1102263
Korean Patent No. 10-1053429

DISCLOSURE

Technical Problem

An object of the present invention is to provide a *Corynebacterium glutamicum* mutant strain having increased L-citrulline productivity.

Another object of the present invention is to provide a method of producing L-citrulline using the mutant strain.

Technical Solution

The present inventors have conducted studies to develop a novel mutant strain having increased L-citrulline productivity using a *Corynebacterium glutamicum* strain, and as a result, have found that, when a mutation is introduced into the NCgl2657 gene encoding an enzyme involved in the production of 6-acetylornithine, which is produced as a by-product in the L-citrulline biosynthetic pathway, or when the NCgl2657 gene is removed, the activity of the enzyme is weakened or inactivated, which not only significantly reduces the production of 6-acetylornithine but also increases the production of L-citrulline, thereby completing the present invention.

One aspect of the present invention provides a *Corynebacterium glutamicum* mutant strain in which the activity of a protein that is expressed by NCgl2657 gene has been weakened or inactivated and which has increased L-citrulline productivity.

As used herein, the term "NCgl2657 gene" refers to a gene encoding the enzyme phosphate acetyltransferase that produces acetyl phosphate, a precursor of acetylornithine, using acetyl-CoA and phosphate as substrates in the L-citrulline biosynthetic pathway.

According to one embodiment of the present invention, the NCgl2657 gene may be derived from a *Corynebacterium* sp. strain. Specifically, the *Corynebacterium* sp. strain may be *Corynebacterium glutamicum, Corynebacterium crudilactis, Corynebacterium deserti, Corynebacterium callunae, Corynebacterium suranareeae, Corynebacterium lubricantis, Corynebacterium doosanense, Corynebacterium efficiens, Corynebacterium uterequi, Corynebacterium stationis, Corynebacterium pacaense, Corynebacterium singulare, Corynebacterium humireducens, Corynebacterium marinum, Corynebacterium halotolerans, Corynebacterium spheniscorum, Corynebacterium freiburgense, Corynebacterium striatum, Corynebacterium canis, Corynebacterium ammoniagenes, Corynebacterium renale, Corynebacterium pollutisoli, Corynebacterium imitans, Corynebacterium caspium, Corynebacterium testudinoris, Corynebacterium pseudopelargi*, or *Corynebacterium flavescens*, without being limited thereto.

According to one embodiment of the present invention, the NCgl2657 gene may be represented by the nucleotide sequence of SEQ ID NO: 1.

As used herein, "weakened activity" means that the expression level of a gene of interest has decreased compared to the original expression level. The term "weakened activity" also includes: a case in which the activity of the protein itself has decreased compared to the activity of the protein in the parent microorganism due to substitutions, insertions, deletions or combinations thereof, of one or more nucleotides in the nucleotide sequence encoding the gene; a case in which the overall activity of the enzyme in the cell is lower than that in the wild-type strain, or the strain before modification, due to decreased expression or translation of the gene encoding the enzyme; and a combination thereof.

As used herein, "inactivated" means that a gene encoding a protein such as an enzyme, a transcription factor or a transport protein is not expressed at all compared to that in the wild-type strain, or the strain before modification, or that the gene has no activity even though it is expressed.

According to one embodiment of the present invention, the weakening or inactivation of the activity of the protein that is expressed by the NCgl2657 gene may be achieved by insertions, substitutions, deletions, or combinations thereof, of all or a portion of the NCgl2657 gene.

As used herein, the term "portion" means not all of the nucleotide sequence or polynucleotide sequence, and may be 1 to 300, preferably 1 to 100, more preferably 1 to 50 nucleotides, without being limited thereto.

According to one embodiment of the present invention, weakening or inactivation of the activity of the protein that is expressed by the NCgl2657 gene may be achieved by inducing a mutation in the start codon of the NCgl2657 gene.

More specifically, the mutation in the start codon of the NCgl2657 gene may be replacement of the start codon ATG of the NCgl2657 gene with another codon, such as TTG or GTG.

In one example of the present invention, the start codon ATG in the nucleotide sequence of SEQ ID NO: 1 encoding the NCgl2657 gene of a *Corynebacterium glutamicum* strain was replaced with TTG, thereby obtaining a *Corynebacterium glutamicum* mutant strain having the new start codon in the NCgl2657 gene. This *Corynebacterium glutamicum* mutant strain may contain the NCgl2657 gene encoded by the nucleotide sequence of SEQ ID NO: 2.

In addition, according to one embodiment of the present invention, weakening or inactivation of the activity of the protein that is expressed by the NCgl2657 gene may be achieved by removing or deleting the NCgl2657 gene.

In one example of the present invention, the NCgl2657 gene in a *Corynebacterium glutamicum* strain was deleted, thereby obtaining a *Corynebacterium glutamicum* mutant strain which has increased L-citrulline productivity and in which the production of the by-product acetylornithine significantly decreases, compared to a wild-type *Corynebacterium glutamicum* strain or a *Corynebacterium glutamicum* mutant strain previously developed to overproduce citrulline.

As used herein, the term "increased productivity" means that L-citrulline productivity has increased compared to that in the parent strain. The term "parent strain" refers to a wild-type strain or mutant strain to be mutated, and includes a strain that is to be mutated directly or to be transformed with a recombinant vector or the like. In the present invention, the parent strain may be a wild-type *Corynebacterium glutamicum* strain or a strain mutated from the wild-type strain.

According to one embodiment of the present invention, the parent strain may be *Corynebacterium glutamicum* ATCC13032.

According to one embodiment of the present invention, the *Corynebacterium glutamicum* mutant strain having increased L-citrulline productivity exhibits increased L-citrulline productivity compared to the parent strain as a result of introducing a mutation in the start codon of the NCgl2657 gene or removing the NCgl2657 gene. In particular, the concentration of L-citrulline produced by the *Corynebacterium glutamicum* mutant strain is at least 5%, specifically 5 to 50%, more specifically 10 to 30% higher than that produced by the parent strain or a previously developed *Corynebacterium glutamicum* mutant strain, while the concentration of 6-acetylornithine produced as a by-product is at least 20%, specifically 20 to 100%, more specifically 30 to 100% lower than that produced by the parent strain or the previously developed *Corynebacterium glutamicum* mutant strain.

The *Corynebacterium glutamicum* mutant strain according to one embodiment of the present invention may be obtained through either a recombinant vector comprising a variant in which the start codon of the NCgl2657 gene in the parent strain has been mutated, or a recombinant vector for deletion of the NCgl2657 gene.

As used herein, the term "variant" refers to a genetic variant in which the start codon ATG of the NCgl2657 gene involved in the biosynthesis of L-citrulline has been replaced with TTG.

As used herein, the term "vector" refers to an expression vector capable of expressing a protein of interest in a suitable host cell, and means a gene construct that contains essential regulatory elements operably linked so that an inserted gene is expressed. As used herein, the term "operably linked" means that a gene to be expressed and the regulatory sequence thereof are functionally linked to each other in a manner enabling gene expression. The term "regulatory elements" includes a promoter for initiating transcription, any operator sequence for controlling transcription, a sequence encoding suitable mRNA ribosome binding sites, and a sequence for controlling termination of transcription and translation. Examples of this vector include, but are not limited to, plasmid vectors, cosmid vectors, bacteriophage vectors, and viral vectors.

As used herein, the term "recombinant vector" refers to a recombinant vector that may be transformed into a suitable host cell, and then may replicate regardless of the genome of the host cell or may be integrated into the genome itself. In this case, the "suitable host cell" may contain a replication origin, which is a particular nucleotide sequence in which replication is initiated so that the vector is replicable.

As used herein, the term "transformation" means introducing a gene into a host cell so that the gene may be expressed in the host cell. The transformed gene may include any gene, regardless of whether the gene is inserted into the chromosome of the host cell or located outside of the chromosome, as long as the gene may be expressed in the host cell. According to one embodiment of the present invention, the transformation method includes any method of introducing a nucleic acid into a cell, and may be performed using a suitable standard technique known in the art, selected depending on the host cell. Examples of the transformation method include, but are not limited to, electroporation, calcium phosphate ($CaPO_4$) precipitation, calcium chloride ($CaCl_2$)) precipitation, microinjection, polyethylene glycol (PEG) method, DEAE-dextran method, cationic liposome method, and lithium acetate-DMSO method. According to one embodiment of the present invention, as the transformation method, an electroporation method (van der Rest et al., Appl. Microbiol. Biotechnol., 52, 541-545, 1999) may be used.

The host cell includes a cell transfected, transformed, or infected with the recombinant vector or polynucleotide of the present invention in vivo or in vitro. The host cell including the recombinant vector of the present invention is a recombinant host cell, a recombinant cell, or a recombinant microorganism.

In addition, the recombinant vector according to the present invention may contain a selection marker. The selection marker is used to select transformants (host cells) transformed with the vector. Since only cells expressing the selection marker can survive in a medium treated with the selection marker, it is possible to select the transformed cells. Representative examples of the selection marker include, but are not limited to, kanamycin, streptomycin, chloramphenicol, and the like.

Genes inserted into the recombinant vector for transformation according to the present invention may be integrated into a host cell such as a microorganism, for example, a *Corynebacterium* sp. strain or *E. coli*, by homologous recombination crossover.

According to one embodiment of the present invention, the host cell may be a *Corynebacterium* sp. strain, for example, a *Corynebacterium glutamicum* strain.

Another aspect of the present invention provides a method for producing L-citrulline comprising steps of: a) culturing the *Corynebacterium glutamicum* mutant strain in a medium; and b) recovering L-citrulline from the cultured mutant strain or the medium in which the mutant strain has been cultured.

The culturing may be performed using a suitable medium and culture conditions known in the art, and any person skilled in the art may easily adjust and use the medium and the culture conditions. Specifically, the medium may be a liquid medium, without being limited thereto. Examples of the culturing method include, but are not limited to, batch culture, continuous culture, fed-batch culture, or a combination thereof.

According to one embodiment of the present invention, the medium should meet the requirements of a specific strain in a proper manner, and may be appropriately modified by a person skilled in the art. For the culture medium for the *Corynebacterium* sp. strain, reference may be made to, but not limited to, a known document (Manual of Methods for General Bacteriology, American Society for Bacteriology, Washington D.C., USA, 1981).

According to one embodiment of the present invention, the medium may contain various carbon sources, nitrogen sources, and trace element components. Examples of carbon sources that may be used include: saccharides and carbohydrates such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid. These substances may be used individually or as a mixture, without being limited thereto. Examples of nitrogen sources that may be used include peptone, yeast extract, meat extract, malt extract, corn steep liquor, soybean meal, urea, or inorganic compounds such as ammonium sulfate, ammonium chloride, ammonium phosphate, ammonium carbonate, and ammonium nitrate. The nitrogen sources may also be used individually or as a mixture, without being limited thereto. Examples of phosphorus sources that may be used include, but are not limited to, potassium dihydrogen phosphate or dipotassium hydrogen phosphate or the corresponding sodium-containing salts. In addition, the culture medium may contain, but is not limited to, metal salts such as magnesium sulfate or iron sulfate, which are required for growth. In addition, the culture medium may contain essential growth substances such as amino acids and vitamins. Moreover, suitable precursors may be used in the culture medium. The medium or individual components may be added to the culture medium batchwise or in a continuous manner by a suitable method during culturing, without being limited thereto.

According to one embodiment of the present invention, the pH of the culture medium may be adjusted by adding compounds such as ammonium hydroxide, potassium hydroxide, ammonia, phosphoric acid and sulfuric acid to the microorganism culture medium in an appropriate manner during the culturing. In addition, during the culturing, foaming may be suppressed using an anti-foaming agent such as a fatty acid polyglycol ester. Additionally, to keep the culture medium in an aerobic condition, oxygen or an oxygen-containing gas (for example, air) may be injected into the culture medium. The temperature of the culture medium may be generally 20° C. to 45° C., for example, 25° C. to 40° C. The culturing may be continued until a desired amount of a useful substance is produced. For example, the culturing time may be 10 hours to 160 hours.

According to one embodiment of the present invention, in the step of recovering L-citrulline from the cultured mutant strain or the medium in which the mutant strain has been cultured, the produced L-citrulline may be collected or recovered from the medium using a suitable method known in the art depending on the culture method. Examples of the method for recovering L-citrulline that may be used include, but are not limited to, centrifugation, filtration, extraction, spraying, drying, evaporation, precipitation, crystallization, electrophoresis, fractional dissolution (e.g., ammonium sulfate precipitation), chromatography (e.g., ion exchange, affinity, hydrophobicity and size exclusion), and the like.

According to one embodiment of the present invention, the step of recovering L-citrulline may be performed by centrifuging the culture medium at a low speed to remove biomass and separating the obtained supernatant through ion-exchange chromatography.

According to one embodiment of the present invention, the step of recovering L-citrulline may include a process of purifying L-citrulline.

Advantageous Effects

The *Corynebacterium glutamicum* mutant strain according to the present invention is capable of producing L-citrulline in high yield and high concentration while inhibiting the production of by-products, because the activity of the protein expressed by the NCgl2657 gene therein has been weakened or inactivated.

MODE FOR INVENTION

Hereinafter, the present invention will be described in more detail. However, these descriptions are provided for illustrative purposes only to aid in the understanding of the present invention, and the scope of the present invention is not limited by these illustrative descriptions.

Example 1. Construction of *Corynebacterium glutamicum* Mutant Strain

In order to construct a *Corynebacterium glutamicum* mutant strain in which the activity of the protein that is expressed by the NCgl2657 gene has been weakened, *Corynebacterium glutamicum* ATCC13032 and *E. coli* DH5a (HIT Competent Cells™, Cat No. RH618) were used.

The *Corynebacterium glutamicum* ATCC13032 was cultured in CM-broth medium (pH 6.8) containing, per liter of distilled water, 5 g of glucose, 2.5 g of NaCl, 5.0 g of yeast extract, 1.0 g of urea, 10.0 g of polypeptone, and 5.0 g of beef extract, at a temperature of 30° C.

The *E. coli* DH5a was cultured on LB medium containing, per liter of distilled water, 10.0 g of tryptone, 10.0 g of NaCl, and 5.0 g of yeast extract, at a temperature of 37° C.

The antibiotic kanamycin obtained from Sigma was used, and DNA sequencing was performed by Macrogen Co., Ltd.

1-1. Construction of Recombinant Vector

Chromosomal DNA was extracted from *Corynebacterium glutamicum* ATCC13032 using the Wizard Genomic DNA Purification Kit (Promega, USA). Using the extracted DNA as a template, PCR was performed using each of a set of primers 1 and 2 and a set of primers 3 and 4. The obtained PCR products were amplified again by crossover PCR using a set of primers 1 and 4 and then inserted into Hindlll and Xbal restriction enzyme sites of the recombinant vector pK19mobSacB. The resulting vector was named pK19 ms/NCgl2657(A1T). For construction of the vector, the primers shown in Table 1 were used.

TABLE 1

| Primer | Primer sequence (5'→3') | SEQ ID NO. |
|---|---|---|
| Primer 1 | ctatgaccatgattacgccacagtggagaacacgatcgcg | 3 |
| Primer 2 | gaggtcggtgtgtcagacaaacatcgcctttctaatttca | 4 |
| Primer 3 | tgaaattagaaaggcgatgtttgtctgacacaccgacctc | 5 |
| Primer 4 | gctcggtacccggggatcctcggcgtcgccgttgtggacc | 6 |

Using the above-described primers, PCR was performed under the following conditions. PCR was performed using a thermocycler (TP600, TAKARA BIO Inc., Japan) in a reaction solution containing 100 μM of each deoxynucleotide triphosphate (dATP, dCTP, dGTP, dTTP), 1 μM of oligonucleotide, 10 ng of the chromosomal DNA of *Corynebacterium glutamicum* ATCC13032 as a template, and 1 unit of PrimeSTAR Max DNA polymerase (Takara, Japan). PCR was performed for 25 to 30 cycles, each consisting of (i) denaturation at 94° C. for 30 sec, (ii) annealing at 58° C. for 30 sec, and (iii) extension at 72° C. for 1 to 2 min (a polymerization time of 2 min per kb).

The gene fragment prepared as described above was cloned into a pK19mobSacB vector by self-assembly cloning. The vector was transformed into *E. coli* DH5a which was then plated on an LB-agar plate containing 50 μg/ml of kanamycin, and cultured at 37° C. for 24 hours. The finally formed colony was isolated and whether the insert was exactly present in the vector was checked. Next, the vector was isolated and used for recombination of the *Corynebacterium glutamicum* strain.

As a process commonly performed in the above method, the corresponding genes were amplified by PCR from the genomic DNA of *Corynebacterium glutamicum* ATCC13032 and inserted into the pK19mobSacB vector by the self-assembled cloning method according to the strategy, and the resulting plasmid was selected in *E coli* DH5a. In this case, in order to insert the amplified gene into the pK19mobSacB vector, a DNA ligation kit (Takara, Japan) and restriction enzymes Hindlll and Xbal (NEB, USA) were used according to the manufacturer's provided buffers and protocols.

1-2. Construction of Mutant Strain

A CT2 strain, a *Corynebacterium glutamicum* mutant strain, was constructed using the pK19 ms/NCgl2657(A1T) vector.

The vector was prepared at a final concentration of 1 μg/μl or more and introduced into *Corynebacterium glutamicum* ATCC13032 by primary recombination using electroporation (see Tauch et al., FEMS Microbiology letters 123 (1994) 343-347). At this time, the electroporated strain was plated on 2YT-Km solid medium (containing 16 g/L tryptone, 10 g/L yeast extract, 5 g/L NaCl, 1.5% agar, and 30 pig/ml kanamycin). The cells were cultured at 30° C. for 2 days to obtain colonies. Among the colonies in which primary homologous recombination was induced, colonies in which amplification was confirmed by PCR using primers 1 and 4 of Table 1 above under the same conditions as in Example 1-1 above were selected as primary recombinant strains and cultured in 2YT liquid medium (containing 16 g/L tryptone, 10 g/L yeast extract and 5 g/L NaCl) for 12 hours. Next, the cultured colonies were plated on 2YT-10% sucrose solid medium (containing 16 μg/L tryptone, 10 g/L yeast extract, 5 g/L NaCl, 1.5% agar, and 100 μg/L sucrose) to induce secondary homologous recombination, thus removing the antibiotic marker. A strain that was not resistant to kanamycin and could grow in the 10% sucrose medium was finally selected. Whether a mutation was introduced into the start codon of the NCgl2657 gene was checked by sequencing (see Schafer et al., Gene 145 (1994) 69-73). Finally, a *Corynebacterium glutamicum* mutant strain (CT2) into which the mutated NCgl2657 gene has been introduced was obtained.

Example 2. Construction of *Corynebacterium glutamicum* Mutant Strain

To construct a NCgl2657 gene-deleted *Corynebacterium glutamicum* mutant strain, wild-type *Corynebacterium glutamicum* ATCC13032 and *E. coli* DH5a were used.

The *Corynebacterium glutamicum* ATCC13032, *E. coli* DH5a, and antibiotic were the same as those used in Example 1.

2-1. Construction of Vector

A vector was constructed in the same manner as in Example 1, except that primers 5 and 6 were used instead of primers 1 and 2, and primers 7 and 8 were used instead of primers 3 and 4. The constructed vector was named pK19 ms/ΔNCgl2657, and the primers shown in Table 2 below were used to construct the vector.

TABLE 2

| Primer | Primer sequence (5'→3') | SEQ ID NO. |
|---|---|---|
| Primer 5 | ctatgaccatgattacgccacagtggagaacacgatcgcg | 7 |
| Primer 6 | caaaacaagtgccaatgccaacatcgcctttctaatttca | 8 |
| Primer 7 | tgaaattagaaaggcgatgttggcattggcacttgttttg | 9 |
| Primer 8 | gctcggtacccggggatcctatcgatgctcatgccagcgg | 10 |

2-2. Construction of Mutant Strain

CT3 strain, a *Corynebacterium glutamicum* mutant strain, was constructed in the same manner as in Example 1, except that the pK19 ms/β vector was used instead of the pK19 ms/NCgl2657(AlT) vector. A strain that was not resistant to kanamycin and could grow in the 10% sucrose medium was finally selected. Whether the NCgl2657 gene was removed was finally checked by performing PCR under the same conditions as in Example 1 using primers 5 and 8 of Table 2 above. The NCgl2657 gene-deleted strain was named CT3.

Comparative Example 1. *Corynebacterium glutamicum* Mutant Strain

A *Corynebacterium glutamicum* mutant strain that has enhanced activities of ornithine carbamoyltransferase and carbamoyl phosphate synthetase to overproduce citrulline (see Korean Patent Application No. 10-2019-0151321, hereinafter referred to as 'CT1') was used.

The CT1 strain was confirmed to have increased L-citrulline production and fermentation yield compared to *Corynebacterium glutamicum* ATCC13032 used as the parent strain.

Experimental Example 1. Evaluation of L-Citrulline Productivity of Mutant Strain L-citrulline productivity was compared between the NCgl2657 gene-mutated strains (CT2 and CT3 strains) constructed in Examples 1 and 2 and the CT1 strain of Comparative Example 1.

Each strain was inoculated into citrulline seed medium and cultured at 30° C. for 10 hours. Then, 250 mL of each culture was inoculated into 5-L culture medium. When the glucose contained in the initial medium was completely exhausted, an additional medium was added. The compositions of the media used in this experiment are shown in Table 3 below. After completion of culture, each culture was diluted 100-fold with distilled water and filtered through a 0.45-μm filter, and then the concentrations of L-citrulline and the by-product 6-acetylornithine in each strain culture were measured using high-performance liquid chromatography (HPLC) equipped with a column (DionexlonPac™ CS12A) and an ultraviolet detector (195 mm). The results are shown in Table 4 below.

TABLE 3

| | Composition (/L) |
|---|---|
| Citrulline seed medium | 2.67% glucose, 3.14% YPA, 0.1% $KH_2PO_4$, 0.1% $K_2HPO_4$, 10 ppm $MnSO_4$, 10 ppm $FeSO_4$, 100 μg/L biotin, and 200 μg/L thiamin-HCl |
| 5-L culture medium | 8% glucose, 0.08% $MgSO_4$, 16 ppm $FeSO_4$, 8 ppm $MnSO_4$, 1.6 ppm $CuSO_4$, 1.6 ppm $ZnSO_4$, 32 ppm $CaCl_2$, 160 ppb biotin, 8 ppm thiamine-HCl, 0.4% HVP, 0.08% NaCl, 0.22% $KH_2PO_4$, and 2.4% $(NH_4)_2SO_4$ |
| Additional medium | 52% glucose, 0.1% $MgSO_4$, 120 ppm $CaCl_2$, 160 ppb biotin, 16 ppm thiamine-HCl, 0.08% $NH_4H_2PO_4$, and 4.4% $(NH_4)_2SO_4$ |

TABLE 4

| Strain | L-citrulline (%) | 6-acetylornithine (%) |
|---|---|---|
| CT1 | 9.73 | 1.21 |
| CT2 | 11.46 | 0.38 |
| CT3 | 10.92 | 0.01 |

As shown in Table 4 above, it was confirmed that the productions of the by-product 6-acetylornithine by the *Corynebacterium glutamicum* mutant strain CT2, which has weakened activity of the enzyme encoded by the NCgl2657 gene, and the NCgl2657 gene-deleted *Corynebacterium glutamicum* mutant strain CT3, decreased by about 69% and 99%, respectively, compared to that by the previously developed mutant strain CT1, and the L-citrulline productivities of these mutant strains increased by about 17.8% and 12.2%, respectively. These results suggest that, when the activity of the protein that is expressed by the NCgl2657 gene is weakened or inactivated, the L-citrulline productivity of the strain can be increased and the production of by-products can also be significantly decreased, and thus the strain is capable of producing L-citrulline with high purity.

So far, the present invention has been described with reference to the preferred embodiments. Those of ordinary skill in the art to which the present invention pertains will appreciate that the present invention may be embodied in modified forms without departing from the essential characteristics of the present invention. Therefore, the disclosed embodiments should be considered from an illustrative point of view, not from a restrictive point of view. The scope of the present invention is defined by the claims rather than the foregoing description, and all differences within the scope equivalent thereto should be construed as being included in the present invention.

The invention claimed is:

1. A *Corynebacterium glutamicum* mutant strain having a gene that comprises all of the nucleotide sequence of SEQ ID NO: 1 except for a mutation at the position that corresponds to position 1, 2, or 3 of SEQ ID NO:1.

2. The *Corynebacterium glutamicum* mutant strain of claim 1, wherein the gene comprises all of the nucleotide sequence of SEQ ID NO:1 except for a substitution at the position corresponding to position 1 of SEQ ID NO:1, wherein the nucleotide at the position corresponding to position 1 of SEQ ID NO:1 is replaced with T or G.

3. A method for producing L-citrulline comprising steps of:

a) culturing the *Corynebacterium glutamicum* mutant strain of claim 1 in a medium; and b) recovering L-citrulline from the cultured mutant strain or the medium in which the mutant strain has been cultured.

* * * * *